(12) United States Patent
Guzzonato et al.

(10) Patent No.: US 10,365,256 B2
(45) Date of Patent: Jul. 30, 2019

(54) HEATED TRANSFER LINE

(71) Applicant: Thermo Fisher Scientific (Bremen) GmbH, Bremen (DE)

(72) Inventors: Antonella Guzzonato, Bremen (DE); Heinz Mehlmann, Bremen (DE); Hans-Juergen Schlueter, Bremen (DE)

(73) Assignee: Thermo Fisher Scientific (Bremen) GmbH, Bremen (DE)

( * ) Notice: Subject to any disclaimer, the term of this patent is extended or adjusted under 35 U.S.C. 154(b) by 0 days.

(21) Appl. No.: 15/381,383

(22) Filed: Dec. 16, 2016

(65) Prior Publication Data

US 2017/0184552 A1    Jun. 29, 2017

(30) Foreign Application Priority Data

Dec. 18, 2015 (GB) .................................. 1522435.5
Dec. 6, 2016 (GB) .................................. 1620713.6

(51) Int. Cl.
| | | |
|---|---|---|
| *G01N 30/30* | (2006.01) | |
| *B01D 53/02* | (2006.01) | |
| *H01J 49/04* | (2006.01) | |
| *G01N 30/72* | (2006.01) | |
| *H01J 49/10* | (2006.01) | |

(52) U.S. Cl.
CPC .......... *G01N 30/30* (2013.01); *B01D 53/025* (2013.01); *H01J 49/0404* (2013.01); *H01J 49/0468* (2013.01); *G01N 30/7206* (2013.01); *G01N 2030/3038* (2013.01); *G01N 2030/3053* (2013.01); *H01J 49/105* (2013.01)

(58) Field of Classification Search
CPC ............... G01N 30/30; G01N 30/7206; G01N 2030/3038; G01N 2030/3053; H01N 49/0468

See application file for complete search history.

(56) References Cited

U.S. PATENT DOCUMENTS

| | | | |
|---|---|---|---|
| 1,995,302 A | | 3/1935 | Goldstein |
| 4,650,964 A | * | 3/1987 | Vincent .................. G01N 30/30 219/390 |
| 5,702,671 A | * | 12/1997 | Gerstel .................. G01N 30/30 138/142 |
| 5,736,739 A | | 4/1998 | Uber et al. |

(Continued)

FOREIGN PATENT DOCUMENTS

| | | |
|---|---|---|
| CN | 104603613 A | 5/2015 |
| EP | 0152946 B1 | 5/1992 |
| JP | 09-080038 | 3/1997 |

OTHER PUBLICATIONS

"Inertium", AMCX, 2003, http://www.amcx.com/pdfs/siteamcxoverview060103.pdf.*

*Primary Examiner* — Justin N Olamit
(74) *Attorney, Agent, or Firm* — David A. Schell

(57) ABSTRACT

A flexible, foldable light-weight gas chromatography transfer line suitable for connecting a gas chromatograph (GC) to a spectrometer, such as a mass spectrometer or optical spectrometer, in particular to the ion source of the spectrometer, such as an inductively coupled plasma (ICP) ion source. The transfer line has a heating arrangement that allows maintaining an even temperature profile, which improves quality of spectra. The transfer line has low thermal mass and the heating can be controlled with the control unit of the GC.

25 Claims, 12 Drawing Sheets

(56) References Cited

U.S. PATENT DOCUMENTS

| | | | |
|---|---|---|---|
| 5,763,876 A | 6/1998 | Pertinarides et al. | |
| 6,530,260 B1 | 3/2003 | Mustacich et al. | |
| 7,221,861 B1 * | 5/2007 | Hannigan | H01J 49/0422 392/478 |
| 7,928,370 B2 * | 4/2011 | Amirav | H01J 49/049 250/281 |
| 7,958,770 B2 * | 6/2011 | Kyle | G01N 30/30 73/23.41 |
| 8,104,330 B2 * | 1/2012 | Hayashi | G01N 30/30 210/198.2 |
| 8,549,893 B2 * | 10/2013 | McCauley | G01N 30/30 73/23.37 |
| 8,642,952 B2 * | 2/2014 | Jarrell | G01N 30/7206 250/288 |
| 8,759,758 B2 | 6/2014 | Steiner et al. | |
| 8,808,629 B2 | 8/2014 | Gerstel | |
| 9,897,576 B2 * | 2/2018 | Matsuoka | G01N 30/30 |
| 2010/0053605 A1 * | 3/2010 | Ragucci | G01N 21/3504 356/301 |
| 2013/0256523 A1 | 10/2013 | Steiner et al. | |
| 2016/0097748 A1 * | 4/2016 | Hansen | G01N 30/06 73/23.37 |

\* cited by examiner

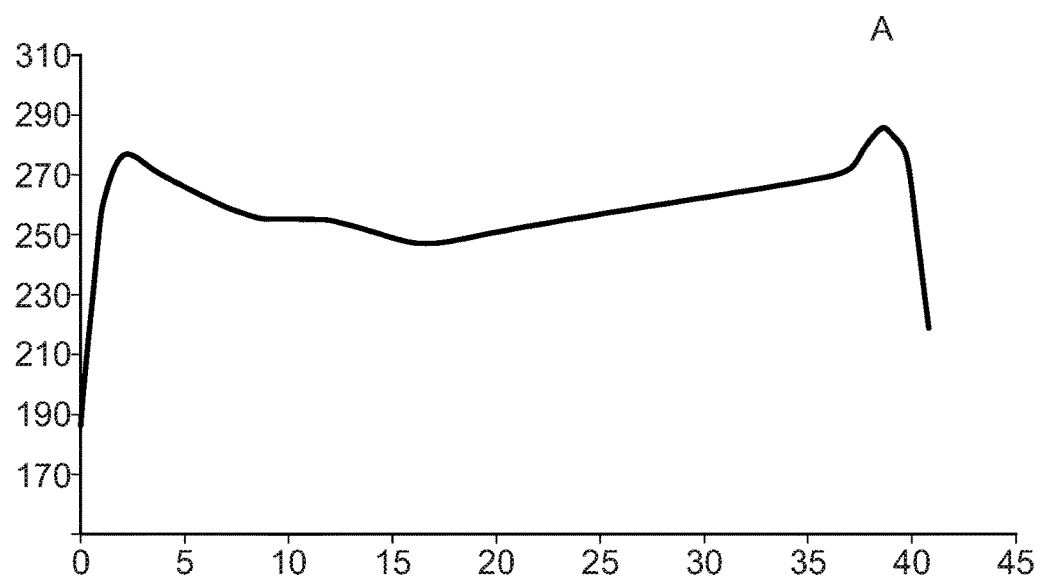
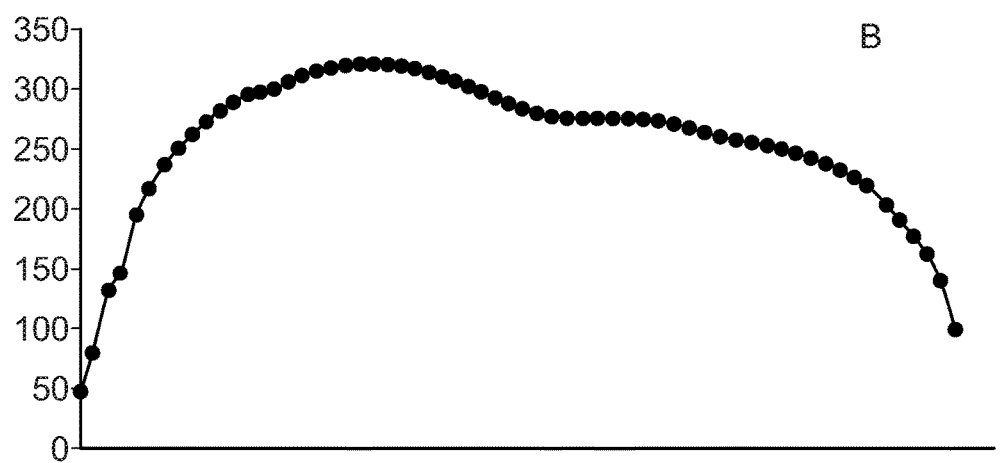
Fig. 5

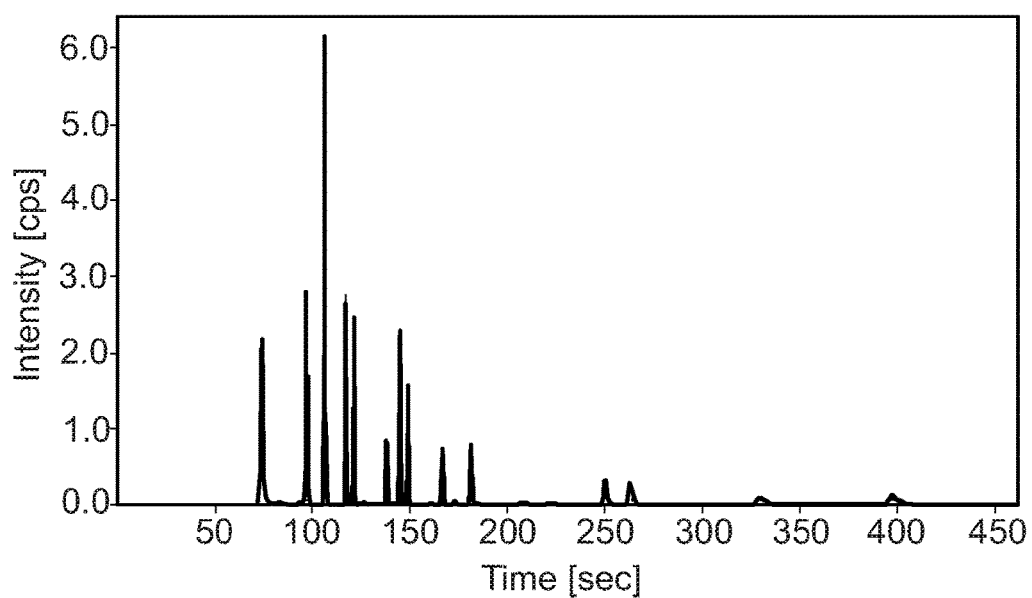
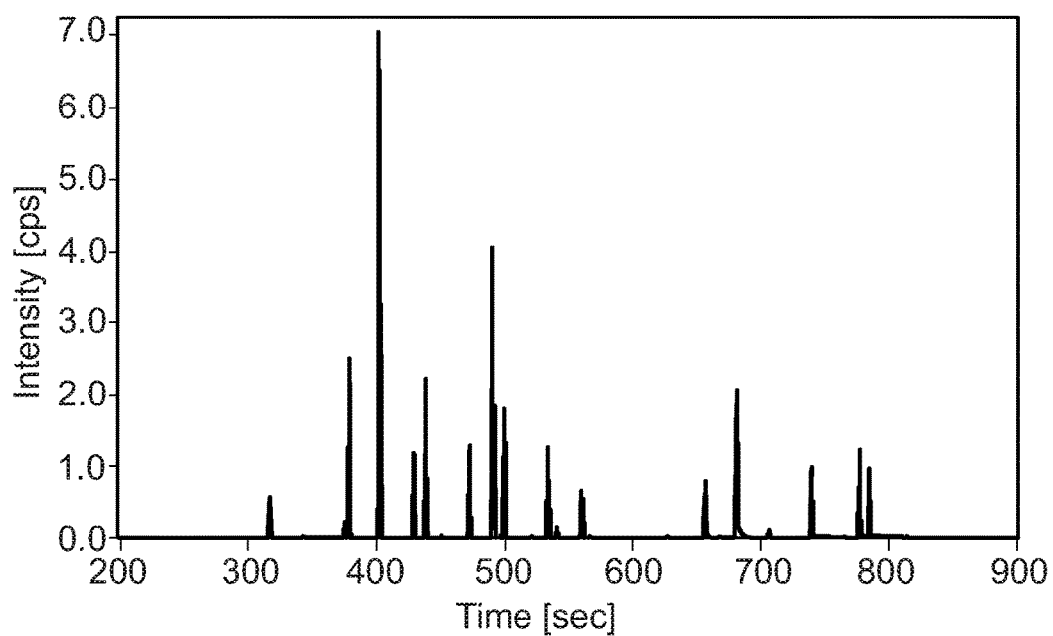
Fig. 8

HEATED TRANSFER LINE

FIELD

The invention relates to heated transfer lines, in particular transfer lines between a gas chromatograph and a mass spectrometer. The invention also relates to GC-MS instruments having heated transfer lines.

INTRODUCTION

Gas chromatography (GC) is a common analytical method for separating and analysing compounds that can be vaporized, usually for determining purity of substances or for separating components of a mixture of substances. In gas chromatography, samples are injected onto a gas chromatography column in a mobile phase, usually an inert gas such as helium. The gas chromatography column typically has a stationary phase that contains a microscopic polymer or liquid layer on an inert solid support.

Compounds that are being analysed interact with the walls of the column, which results in different elution times of the compounds depending on their chemical and physical properties. The dimensions of the column also have an effect on the elution profile. The columns are designed to have different properties that are appropriate for any given analysis, and usually involve variation in polarity of the stationary phase, together with application of specific functional groups.

The GC columns are heated, usually by placing the columns inside an oven. The temperature of the GC column will influence the elution profile, higher temperatures favouring fast elution and less interaction with the stationary phase.

Compounds that elute from the GC column need to be detected to establish a chromatogram. In many applications, the detector is provided by a mass spectrometer, which can separately capture, ionize, accelerate and detect the different compounds that elute from the GC column. The gas chromatography and mass spectrometry methods are complementary in nature, and their combination provides a powerful tool for many analytical applications that require high sensitivity and accuracy.

Compounds that elute from a GC column need to be transferred to the ion source of a downstream mass spectrometer. Typically, the connection between the gas chromatograph and the ion source is a solid, semi-permanent transfer device, adapted to interface with the ion source which can be under vacuum, such as in Electron Impact (EI) mass spectrometry, or at atmospheric pressure, such as in inductively coupled plasma (ICP) mass spectrometry (ICP-MS).

In ICP-MS, the ion source is provided by an inductively coupled plasma that is generated within an ICP torch. The ICP torch is typically made of glass and its position is adjustable in three dimensions for optimization of the plasma conditions. For some applications, mass spectrometers are permanently set up to be used with a gas chromatograph, while in others (such as ICP-MS), connection to a GC instrument may be optional, and used interchangeably with other sample provision systems.

Connections or transfer lines, for connecting GC and MS instruments are known in the art. U.S. Pat. No. 4,650,964 discloses a heated transfer line for heating a glass capillary tube. Power is applied to an electrically conductive heater tube which encircles the glass capillary via first and second current conductors that are attached to respective ends of the heater tube. Electrical insulation is disposed between the heater tube and first and second current conductors, and a cover of thermal insulation is disposed over the heater tube and the current conductors to thermally isolate the heater tube.

U.S. Pat. No. 5,702,671 describes a gas chromatograph transfer line for transporting a sample into a GC column that has a glass tube, a steel tube enclosing the glass tube and a heating coil enclosing the steel tube, and in which a tube made of a material with high thermal conductivity is arranged between the steel tube and the heating coil.

EP 152946 discloses an apparatus for heating a length of tubing, for example a glass capillary tube in gas chromatography. Power for heating the glass capillary tube is applied by passing current through a cylindrical heater tube which encircles the glass capillary tube. The heater tube is encircled by further tubes for electrical and thermal insulation.

U.S. Pat. No. 8,759,758 discloses a transfer line for conveying column effluent from a gas chromatograph to an ion source of a mass spectrometer that has a transfer line body and a mechanism for moving the transfer line body either towards or away from the mass spectrometer. A gas seal between the housing of the mass spectrometer and the transfer line body prevents vacuum leak when the transfer line body is moved.

U.S. Pat. No. 7,958,770 discloses a heat transfer line assembly for microwave heated chromatography instruments. The transfer line can be heated by means of a wire that is wound around a thermally conductive rod. The transfer line is surrounded by a bulky insulating housing.

U.S. Pat. No. 8,808,629 discloses a transfer unit for analysis devices, containing a tube-shaped assembly which can be heated by an electric heater in a programmed manner, and a tube for receiving a gas chromatographic separating column. The unit has a temperature sensor arranged in a ring chamber between the inner wall of the assembly and an evaporator tube.

U.S. Pat. No. 6,530,260 discloses a gas chromatography system that includes a GC oven with a door adapted for integration with gas chromatography modules located outside of the oven, the door having module receiving openings in which the modules are secured. Inside the module housing is a coil of a capillary column, a pair of transfer lines sleeved on the free ends of the capillary column, a heater wire wound on the transfer lines, where the wire may be wound with fewer number of windings per inch along the length of the transfer line toward the oven cavity.

U.S. Pat. No. 5,736,739 discloses a GC-ion mobility spectrometer system having a heated transfer line between the GC and the spectrometer. The transfer line is heated to prevent that analyte species adsorb on the walls on the transfer line. Heating element wires are arranged in a single or dual helix fashion around the transfer line passageway, penetrating through holes in two bonded cylindrical half-sections of insulating material that is embedded between metal shells. To provide a more uniform temperature profile across the length of the passageway the winding density (pitch) of the heating element wires is increased near the heating device inlet and outlet.

It enhances quality of the analysis that during the transfer of effluent from the GC column to a downstream optical spectrometer and/or MS ion source, the temperature be uniformly maintained. Temperature fluctuations during effluent transfer, in particular cold spots, can lead to condensation from the gas phase and/or excessive peak broadening. Further, the GC-MS transfer lines that are known in the art are usually rigidly attached to the housing of the mass spectrometer and the gas chromatograph, which leaves minimal or no means to adjust positioning, for example to an ICP torch.

SUMMARY

The present invention is specified in the claims as well as in the below description.

The invention relates to bridging devices, also called transfer lines, that are used to connect a gas chromatograph (GC) to a spectrometer, such as a mass spectrometer or optical spectrometer, in particular to the ion source of the mass spectrometer. Frequently, such transfer lines are connected to an inductively coupled plasma (ICP) ion source. Common problems that such bridging devices face and ideally should be overcome include: 1) the heat profile along the transfer line should be homogeneous and constant; 2) the transfer line should be flexible enough to allow free movement with minimal resistance on the ICP torch side; and 3) there should be no cold spots that can lead to condensation of analytes and peak broadening as a consequence; 4) there should be no hot spots that can cause decomposition of the analyzed compounds.

The present invention provides a transfer line that overcomes these and other challenges. The transfer line, for transferring a sample from a gas chromatograph into a spectrometer for analysis, has an entry end for connecting to the gas chromatography column and an exit end for connecting with a spectrometer, and comprises:

a flexible transfer capillary for receiving therein an end portion of a gas chromatography column or a capillary connected to said end portion;
at least a first resistive heating arrangement, surrounding the transfer capillary; the resistive heating arrangement being connectable to a power supply for providing current to the heating arrangement or heating layer to heat the heating arrangement or heating layer and thereby heat the transfer capillary;
wherein said first resistive heating arrangement is divided into at least one central zone and at least one exit zone, and wherein the first resistive heating arrangement is adapted to provide different heat emission per unit length in said at least one central zone than in said exit zone,
wherein the flexible transfer line is foldable.

The invention also provides a gas chromatography—mass spectrometry (GC-MS) system, comprising
at least one gas chromatograph,
at least one transfer line,
at least one mass spectrometer,
wherein the at least one transfer line has an entry end that is fluidly connected to the gas chromatograph, and an exit end that is fluidly connected to the mass spectrometer, and wherein the at least one transfer line is as disclosed herein.

The resistive heating arrangement is preferably adapted to provide heat emission for heating the transfer line that compensates for heat dissipation that otherwise would occur from the transfer line. Typically, heat emission from transfer lines is greatest at respective ends, where the transfer line is connected to respective upstream and downstream analytical components, for example an upstream gas chromatograph and a downstream spectrometer (e.g., optical spectrometer or mass spectrometer), which connections can act as heat sinks.

The heating arrangement can comprise electrically resistive material, such that when an electrical current is applied to the heating arrangement, heat is generated and transferred or emitted to the transfer capillary that the heating arrangement or heating layer surrounds.

The resistive heating arrangement can be in the form of a resistive heating layer, which in some embodiments comprises a material that is provided in the form of a carrier sheet or sheath that can surround the transfer capillary. The carrier sheet is preferably adapted so as to provide different heat emission along its length, so as to compensate for greater heat emission at the ends of the transfer line. For example, the carrier sheet can comprise a higher density of resistive material at, or towards, the ends of the transfer line so that when power is applied to the carrier sheet, greater thermal emission per unit length occurs near the ends of the transfer line.

The resistive heating arrangement can comprise one or more resistive wire that surrounds the transfer capillary so that when power is applied to the resistive wire, heat is generated in the wire and dissipated to the transfer capillary, thereby heating it. Preferably, the resistive wire is layered or wound around the transfer capillary so that during operation, there is an approximately uniform temperature in the transfer capillary along its entire length.

Heat emission that is provided by the resistive wire can be regulated by the properties of the wire itself or by the manner in which the wire is wound around the transfer capillary. For example, the pitch of the resistive wire can be varied along the transfer capillary. In this context "pitch" is the distance between adjacent windings (between respective midpoints) measured along the axis of the transfer line, i.e. the width of one whole turn of the wire around the transfer capillary.

By having a smaller pitch (tighter windings) of the wire towards one or both end of the transfer capillary, there can be increased heating at the ends when power is applied to the wire. The pitch of the resistive wire in the central zone can be in the range of about 5% to about 35% greater, more preferably about 10% to about 35%, even more preferably about 15% to 35% greater, than the pitch in the entry zone and the pitch in the exit zone.

The pitch in the central zone can also be in the range of about 15% to about 25% greater than the pitch in the entry zone and the pitch the exit zone.

The length of each of the end zones (exit zone and entry zone respectively) can be 5-10%, e.g. about 5%, of the length of the central zone. In some embodiments, there can be middle zones, for example a middle zone between the entry zone and central zone and a middle zone between the entry zone and central zone. Each middle zone can be 5-10%, e.g. about 5%, of the length of the central zone. The middle zone can have a wire pitch that is intermediate between the pitches of the wire winding in the central zone and its respective end zone that it lies between. For example, the middle zone can have a pitch that is 10% lower than the central zone and the end zone can have a pitch that is 10% lower than the middle zone.

As understood from the above, in many useful embodiments the transfer line has at least one entry zone, adjacent the GC, at least one central zone, and at least one exit zone.

In certain embodiments however, there is not a specific entry zone with different heating applied by resistive heating arrangement or layer, but instead heat dissipation from the entry end is minimized by incorporating a suitable length of the transfer line and/or an extending end of the transfer capillary of the transfer line inside a GC oven or the like heating means of the GC, and using the heat therein to maintain a desired temperature of the entry end of the transfer line.

There can also be two or more entry and/or exit zones, each zone having its own wire winding pattern or pitch. For example the resistive wire winding can comprise at least two entry zones, wherein a first entry zone is more distal from the central zone and a second entry zone is more proximal to the central zone, such that the pitch of the winding in the first entry zone is smaller than the pitch in the second entry zone, which in turn is smaller than the pitch in the central zone.

There can also be at least two exit zones, a first exit zone more distal from the central zone and a second exit zone more proximal to the central zone, such that the pitch of the winding in the first exit zone is smaller than the pitch in the second exit zone, which is smaller than the pitch in the central zone.

In other words, there can be different zones along the length of the transfer capillary, each having its unique winding pattern (pitch) so as to generate variable and distinct heating power along the transfer line.

The different zones can be of any suitable length, e.g. the exit zone and optional entry zone can in some embodiments each be in the range of 5-10% or in the range 10-40% of the total length of the transfer line, such as e.g. 2 cm, 4 cm, 5 cm, 10 cm or 20 cm, respectively. The entry zone(s) can have the same or different length than the exit zone(s). As described in further detail below, the entry end of the transfer line is in some situations extended into the GC oven to which the transfer line connects. In such cases, the transfer capillary within the transfer line may extend further than the heating arrangement, for example, the heating arrangement may be configured so as to enclose the portion of the transfer capillary outside the GC oven and the portion that lies within the wall itself (extending through the bore of the wall) but not enclosing the portion inside of the GC oven wall, when the transfer line is suitably connected to a GC. Such embodiments may have an entry zone as described herein with more heating than in the central zone, where the entry zone is arranged on the distal end of the heating arrangement, such that the entry zone preferably extends into the GC oven wall but not into the cavity of the GC oven.

The resistive wire pitch within each respective zone can in some embodiments be uniform or even. The pitch can however also change gradually within each zone. For example the pitch can be gradually increasing (preferably not increased in discrete steps) along an entry zone from the distal end of the zone to the proximal end of the zone. The pitch can also gradually increase along an exit zone from the distal end of the zone to the proximal end of the zone. The pitch can also be uniform within certain zones and have a gradient within other zones. The gradient of a pitch in any given zone is preferably uniform, i.e. linear, but the gradient of pitch within a zone can also be non-linear, i.e. the increase or decrease in pitch may change linearly or non-linearly.

The pitch at the end of any given zone can be substantially identical to the pitch at the adjacent end of a neighbouring zone. For example, the pitch at the proximal end of an entry zone and the proximal end of an exit zone can the same as the pitch in the central zone adjacent to the entry and exit zones.

The winding pattern of the wire can also be varied in a modular fashion. For example, there can be "pulsed width" modulation of the winding along the transfer capillary, such that a unit coil is repeated at variable distances along the transfer line, thereby leading to different heat emission by the wire. The unit coil can be identical (i.e. contain identical number of windings with identical pitch) or different along the transfer capillary. When different, the space between unit coils can be uniform, but the heat emission along the transfer line will be different due to the fact that each unit coil is different.

Alternatively, or additionally, the resistivity of the wire can be variable. Thereby, even when the wire has a uniform pitch along the transfer capillary, there will be uneven heat emission by the wire due to its variable resistivity. The resistance of the wire in the first entry zone can thus be different (e.g., higher) from the resistance of the wire in the central zone. Where there is more than one entry zone, the resistance of the wire in the first entry zone can thus be different (e.g., higher) from the resistance of the wire in said second entry zone, which in turn can be different (e.g., higher) from the resistance of the wire in the central zone. Similarly, the resistance of the wire in the exit zone can thus be different (e.g., higher) from the resistance of the wire in the central zone. Where there is more than one exit zone, the resistance of the wire in the first exit zone can be different to the resistance of the wire in said second exit zone, which in turn can be different to the resistance of the wire in the central zone. There can also be different type of wire within one or more zone along the transfer line, so as to provide different resistance, leading to different heat emission by the wire for identical power applied. Such variable resistance can also be combined with variable winding pattern, as described in the foregoing.

It is also possible to connect resistance wires within different segments or zones along the transfer capillary separately to different power supplies, or control the power that is applied to each in an independent fashion. In other words, the power to the resistive wire in an entry zone can be independently applied to another resistive wire in the central zone. The power to the resistive wire in an exit zone can also be independently applied to the resistive wire in the central zone. When multiple entry-, central-, and/or exit zones are present, the power to each zone can also be independently applied. In this manner, the heat emission within each such zone can be independently controlled, even in the case where each zone has an identical wire composition and/or pitch.

There can be a second, or even further layers of a resistive heating arrangement that preferably surrounds the first layer. Such further layer or layers can be provided as a buffer to maintain a stable temperature along the transfer line, and can at the same time provide compensation for any temperature fluctuations that are not sufficiently compensated for by the first layer. The second heating arrangement and/or heating layer can be a similar type to the first. Alternatively, they may be of different types, i.e. a heating layer (e.g. sheet) can surround a heating arrangement (e.g. wire), or a heating arrangement (e.g. wire) can surround a heating layer (e.g. sheet).

There can thus be a second winding of resistive wire that surrounds the first winding of resistive wire and which is preferably also wound in spiral fashion around the transfer capillary. The second winding (first layer) can be layered so as to be superimposed on, or on top of, the first winding. The second winding can also be interlaced with the first layer. The second winding can act to smooth the temperature profile of the transfer line further. In a preferred embodiment, the outer second winding is wound with a constant (uniform) pitch, which is preferably larger than the central zone, more preferably 10-20% (more preferably 15%) larger than the central zone of the first winding layer. This second winding layer preferably has a constant pitch so as to act as a heat insulating material producing the desired insulating effect without the unwanted "heat sink" effect of the higher thermal mass carried by conventional insulating material in contact with the actively heated part of the transfer line.

The second layer can have a uniform pitch. The second layer can also have an uneven pitch or a pitch pattern opposite to the first layer (e.g. with the exit and entry zones having a wider pitch than the central zone) or in other ways be implemented so as to provide uneven heat emission along the transfer line, as described in the foregoing for the first layer. In some embodiments, the second layer, e.g. of more uniform pitch than the first layer, can be located underneath, rather than surrounding, the first layer.

The resistive heating arrangement preferably has a relatively stable resistivity over a wide temperature range. Preferably, the heating arrangement has less than 20% variation in resistivity over a wide temperature range, preferably at least in the range of 100 to 400° C., more preferably 200 to 400° C., more preferably 250 to 320° C. even more preferably 300 to 320° C. The resistivity of the resistance wire can be in the range from about 1 Ohm/m to 500 Ohm/m. In some embodiments, the resistivity of the resistance wire can be in the range from about 100 µOhm/cm or from about 120 µOhm/cm, to about 140 µOhm/cm or to about 150 µOhm/cm, more preferably about 130 µOhm/cm. The resistive wire can be made from any suitable resistive material. Preferably, the wire can be made from a Ni—Cr alloy, such as stainless steel or the like.

The resistive material, such as the resistive wires, can be coated with an electrically insulating material or coating, that should withstand the desired temperatures. Exemplary materials include polyimide material, such as Kapton and fluoropolymers such as polytetrafluoroethylene. There can additionally, or alternatively, be an electrically insulating layer or sheath between wire layers or windings. Such an electrically insulating layer can be made of any suitable and flexible material, such as fibreglass, fiber-rock or silicon oxide cured gel.

The skilled person will appreciate that the foregoing features to selectively control heat emission can be combined in any desired fashion within a transfer line. In other words, the different methods or manner described in the foregoing can be used in combination to selectively apply suitable temperature control of the transfer line.

Thermal mass is a property of the mass of an object which enables it to store heat, thereby providing "inertia" against temperature fluctuations.

Thermal mass is equivalent to thermal capacitance or heat capacity, the ability of a body to store thermal energy. It is typically referred to by the symbol $C_{th}$ and measured in units of J/° C. or J/K (which are equivalent). This measure if therefore useful for characterizing the ability of the transfer line to maintain a stable temperature, and the power needed.

In general terms, thermal mass can be defined as:

$$C_{th} = Q/\Delta T$$

where Q is the thermal energy transferred and $\Delta T$ is the change in temperature. The thermal mass of a transfer line according to the present invention, which can be approximated to be constant over the typical operating temperature range, can be estimated in two ways:

a) by an observed heating rate and the applied power. In one configuration, the applied power is 180 W and the temperature ramped from room temperature to 295° C. in 9 s, and as a consequence
P=180 W=180 J/s; and Q=180 J/s*9 s=1620 J
$\Delta T$=(295°−25°)=270°
and therefore
$C_{th}$=1620 J/270=6 [J/K].
For a transfer line having a length of 0.5 m the relevant thermal mass per length will be 12 [J/(K·m)].
For a transfer line with a mass of 25 g, this gives a specific heat capacity of
6 (J/K)/0.025 kg=240 [J/(kg·K)].

b) The total thermal capacity can be estimated as dominated by the specific heat capacity of the base material of the flexible transfer capillary, if stainless steel is used the specific heat capacity is about 450 [J/(kg K)] (other useful metals typically have similar values, e.g. nickel has a specific heat capacity of 440 [J/(kg K)]:
$C_{th}$=450 [J/(kgK)]*0.025 kg=11 [J/K].

Obviously, variations of the transfer line, such as longer transfer lines, transfer lines comprising an inner tube having a different heat capacity, or transfer lines of other thickness, will have a different specific heat and thermal capacity.

The transfer line in general can have a specific heat capacity in the range of from about 100 J/(kg K), such as from about 200 J/(kg K), such as from about 300 J/(kg K), or from about 400 J/(kg K), such as to about 1000 J/(kg K), or to about 800 J/(kg K), such as to about 600 J/(kg K), or to about 500 J/(kg K). The transfer line can have a specific heat that is less than 1000 J/(kg K), less than about 800 J/(kg K), less than about 600 J/(kg K) or less than about 500 J/(kg K).

The transfer line in accordance with the invention has the advantage that its thermal mass is low and thus that it requires relatively little power to be heated. In general, the thermal mass of the transfer line according to the present invention can be less than about 50 J/K, less than about 40 J/K, less than about 30 J/K, less than about 20 J/K, or less than about 15 J/K. The thermal mass of the transfer line can be greater than about 5 J/K, or greater than about 10 J/K. The thermal mass can be in the range of about 5 to about 50 J/K, about 5 to about 40 J/K, about 5 to about 30 J/K, about 5 to about 20 J/K, or in the range of about 5 to about 15 J/K.

The thermal mass per unit length of the transfer line can be less than about 100, less than about 50, less than about 40, less than about 30, or less than about 25 [J/(K·m)]. The thermal mass per unit length can also be in the range of about 5 to 30, more preferably in the range of about 10 to 25 [J/(K·m)].

The transfer capillary is preferably chemically inert, at least on its inner surface, so as to avoid undesired chemical reactions between the capillary and samples that are passed through the transfer line from a GC column. Accordingly, the transfer capillary can be coated on at least its inner surface by a suitable inert material. The transfer capillary can comprise a metal tubing (e.g. nickel tubing) with an inert coating on its inner surface. The inert coating can be a silicon based coating, including sulfinert, or other glassy coatings, or a polymer coating. Preferably, the coating is, or comprises, a polyimide coating, such as Kapton or Vespel.

The flexible transfer capillary is preferably adapted to receive a GC column such that the GC column terminates within one of the heated zones of the flexible transfer capillary. The transfer capillary can also receive an inert capillary that is connected to a GC column. The capillary can terminate at or near the end of the heated zones, within the central zone, or within the entry zone. Preferably, the GC column, or an inert capillary connected thereto, terminates about 1 cm to about 5 cm, preferably about 1 cm to about 3 cm, more preferably about 2 cm from the distal end of the entry zone.

The flexible transfer capillary can further be adapted to connect at or near its entry end to a supply of inert carrier gas, preferably argon, such that the carrier gas can flow in the space (interspace) between the transfer capillary and an inserted GC column in a direction towards the exit end of the transfer capillary. This way, samples that are passed through the GC column will flow from the end of the GC column into the transfer capillary, wherein they are carried by the stream of carrier gas towards a downstream spectrometer. The carrier gas can be the plasma forming gas of the ICP ion source (e.g. Argon, Helium or Hydrogen) or any process gas of the device downstream of the capillary. Typically, in the interspace between the GC column and the transfer capillary a sheath argon gas flows into an ICP ion source together with the He from the GC column.

The resistive heating arrangement can surround the transfer capillary along substantially its entire length. The heating arrangement can also terminate at a predetermined distance from the entry end of the transfer line so that, during operation, the part of the transfer capillary that is not enclosed by the heating arrangement is positioned within the oven of a gas chromatograph to which the transfer line is connected. This way, the part of the transfer capillary that is not heated by the resistive heating arrangement is heated by the GC oven, and thus maintained at an appropriate temperature. The resistive heating arrangement can for example terminate at a distance in the range of about 1 cm to about 20 cm, or about 2 cm to about 15 cm, from the entry end of the transfer line. The transfer line is designed to span a distance from the GC, outside of the GC oven, to an inlet of a mass spectrometer.

The flexible transfer capillary can have an inner diameter in the range of about 0.40 mm to about 1.0 mm and an outer diameter in the range of about 1.0 mm to about 2.5 mm. The transfer line, including the heating arrangement can have an outer diameter in the range of about 1.5 mm to about 5 mm.

The transfer line can further comprise an outer electrically insulating and/or heat insulating sleeve along at least a portion thereof. The outer diameter of the transfer line, including such insulating sleeve, can be in the range of about 2.0 to about 10 mm, preferably about 2.0 to about 5 mm. The outer sleeve can protect a user from contacting resistance wire when current is flowing through it. Furthermore, the transfer line could be positioned under a protective hood or cover to protect the user from the hot surface of the transfer line. The hood or cover preferably is rigid and/or preferably is spaced apart from the transfer line.

The transfer line can have an overall length in the range from about 20 cm, such as from about 30 cm, such as from about 40 cm, to about 100 cm, or to about 80 cm, such as to about 70 cm, even more preferably about 50 cm.

The gas chromatography transfer line is very flexible, allowing for easy folding away or bending of the transfer line, without putting severe strain on the line or without the line breaking. Here the term "flexible" refers to the function of the transfer line itself. In use, for example for interfacing the transfer line with a movable ICP torch or another movable component of a mass spectrometer, it is required that the transfer line can be flexed during use, at least during initial set-up e.g. tuning or aligning of the ICP torch. The transfer line is preferably flexible enough that it is foldable, thereby putting little or no strain (substantially no strain) on an ICP source when connected at its exit end to the ICP source and the ICP source is moved, typically moved in 3 dimensions. Preferably, the transfer line has a bending radius of less than about 40 mm, more preferably less than about 35 mm, more preferably less than about 30 mm, more preferably less than about 25 mm, more preferably less than about 20 mm, more preferably less than about 15 mm and even more preferably less than about 12 mm. The term bending radius as used herein refers to the minimum radius (measured to the inside curvature) by which the transfer line can be bent without any damage such as kinking. Thus a low bending radius indicates greater flexibility.

The transfer line is also light, thereby putting little strain on the components to which it is attached. Preferably, the transfer line has a weight of less than about 100 g, preferably less than about 50 g, and more preferably less than 30 g. Obviously, the weight of the transfer line depends on its length. However, one advantage of the transfer line is its low density. Preferably, the transfer line has a weight per unit length of less than about 200 g/m, preferably less than about 100 g/m, and more preferably less than 50 g/m.

One or more temperature sensors can be attached to, or be a part of, the transfer line, to provide feedback about the actual temperature of, or within, the transfer line. Preferably, the temperature sensor is positioned so as to be in contact with the transfer capillary. Ideally, such a temperature sensor is placed within the transfer capillary. Such a temperature sensor can provide feedback to a temperature control unit. The temperature control unit preferably can comprise a computer or processor and can use software to control the power supply based on the temperature feedback. The temperature control unit can be interfaced to the power supply/supplies that provide power to the resistive heating arrangement, so as to control the output of the power supply to the resistive heating arrangement and thereby control the temperature of the flexible transfer capillary.

The temperature control unit and the power supply can be part of an oven control unit for controlling the temperature of a GC oven in which the GC column is housed. Thereby, the same control unit can be used to control temperature in the GC oven and in the transfer capillary. It can be preferable that the temperature of the GC oven and the transfer capillary be identical or nearly identical. The oven control unit can therefore be operable to simultaneously ramp the temperature of the flexible transfer capillary and the temperature of the GC oven. Thus, the heating of the transfer line can be adapted to change the temperature of the transfer capillary substantially simultaneously with corresponding temperature changes of the GC system to which the transfer line is connected. The oven control unit can be operable to control the temperature of the transfer capillary and GC oven so that, in use, the two have substantially the same temperature. In one embodiment, temperature changes of the GC system are controlled by the programmed temperature vaporizing (PTV) unit of the GC, which thereby serves as the oven control unit. In one embodiment, the GC system is able to control the programmed temperature vaporizing (PTV) unit, which in some embodiments follows the temperature ramp of the GC oven. Preferably, the difference in temperature of the two (GC oven and transfer capillary) is within about 40° C., more preferably within about 30° C., even more preferably within about 20° C., and yet more preferably within about 10° C. and most preferably within about 5° C. In contrast, in the prior art GC-MS transfer lines there is a lack of software control of heating and a physical impossibility to have a transfer line that responds to temperature changes of the GC oven promptly enough to effectively be at the same temperature as the GC oven during a ramped GC temperature program: the ability to heat up and cool down rapidly is depending on the low thermal mass of the transfer line of the invention.

It can be preferable that the oven control unit controls the temperature of the transfer capillary so that its temperature is in the range of about 30° C. lower to about 10° C. higher than that of the GC oven, preferably about 30° C. lower to about the same as that of the GC oven.

The transfer line has the advantage that its temperature can be ramped quickly, and its temperature maintained essentially constant along its length. Thus, the transfer line and the temperature controller to which it is connected can be adapted to ramp the temperature of the transfer line at a rate that is in the range of about 10° C./min to about 200° C./min, preferably about 10° C./min to about 100° C./min, more preferably about 10° C./min to about 60° C./min.

The transfer line can be heated to and maintained at a temperature within a temperature range comprising at least the range from about 50° C. to about 350° C., preferably about 200° C. to about 320° C., wherein the transfer line is capable of maintaining a temperature profile over at least 90% of its length with less than ±5% variation in temperature.

More preferably, the transfer line can be heated to and maintained at a temperature within a temperature range comprising at least the range from about 50° C. to about 350° C., preferably about 200° to about 320° C., wherein the transfer line is capable of maintaining a temperature profile over at least 95% of its length with less than ±15% variation, more preferably less than ±10% variation, even more preferably less than ±5% variation, even more preferably ±3% in temperature.

Further, the transfer line can be heated to and maintained at a temperature within a temperature range comprising at least the range from about 200° to about 320° C., wherein the transfer line is capable of maintaining a temperature profile over its length, preferably over at least 95% of its length, more preferably over all of its length surrounded by the resistive arrangement or layer, with a relative standard deviation (RSD) less than 20%, preferably less than 15%, more preferably less than 10%.

The transfer line according to the invention is useful for transferring gaseous samples between individual components of analytical systems. The transfer line is particularly useful for transferring effluent (comprising carrier and eluting sample components) from a gas chromatograph to a downstream spectrometer. The spectrometer can for example be an optical spectrometer or a mass spectrometer. The transfer line can therefore be adapted to connect through its entry end to a gas chromatography column and through its exit end to a mass spectrometer or optical spectrometer. In particular, the transfer line can, at an exit end of the transfer capillary, be adapted to connect to an inductively coupled plasma (ICP) ion source, preferably an ICP source of a mass spectrometer or an optical spectrometer. The advantage of the transfer line being light-weight and flexible is a distinct advantage for such configurations, since risk of causing damage to the ICP torch of the ICP source or its motor during movement of the torch is minimized.

Accordingly, the transfer line can be connected to an ICP ionisation source that comprises an ICP torch that is moveable by a motor drive in three dimensions (x, y, z), with the z direction being generally the axial direction of the transfer line and the x, y axes being perpendicular to z. The movement range of the ICP motor drive can be, for example, in the range of 2-20 mm along any of the three dimensions x, y, z. For example, the movement range can be up to about 10-20 mm, preferably up to about 15 mm, along the z direction, and up to about 2-6 mm, preferably up to about 4 mm, along the x and y directions. The transfer line can have a force of displacement of the exit end of the transfer line, when remaining parts of the transfer line are fixed, that is matched to be less than the actuation force of the motor. The displacement force in each dimension (x, y, z) (force needed by a motor to move, lift or bend the transfer line exit end when the entry end is fixed) can be less than about 10 N, less than about 5 N, less than about 2 N, less than about 1 N, less than about 0.5 N. Preferably, the displacement force is less than about 2 N, more preferably less than about 1.5 N, even more preferably less than about 1 N yet more preferably less than about 0.5 N.

The flexibility of the transfer line thus allows three-dimensional movement of the line and in particular of the exit end, when the entry end is connected to a GC interface (i.e. raising, lowering, moving left or right the exit end, and also including moving the exit end in the direction away from or towards the GC oven, and any combination of the above general movement directions, and also including folding the transfer line into a "curvy" shape or "spring" shape. As mentioned, any such movement is preferably accomplished with a low force of displacement, such as within a value mentioned above. Typically, as mentioned above, movement of the exit end of the transfer line in GC MS arrangement when the entry end is connected to a gas chromatograph can be provided by three orthogonal motors mounted at the mass spectrometer injector (receiving the transfer line exit end) with a displacement force that is preferably lower 1N in each direction.

There is also provided a method of manufacturing a gas chromatography transfer line, in particular a transfer line comprising a resistive wire, as described in the foregoing. The method can comprise steps of
a. providing a transfer capillary and at least one resistance wire to be wound around the transfer capillary;
b. dispensing the resistance wire onto the transfer capillary at a dispensing point, while simultaneously rotating the transfer line at a constant rotational speed;
wherein the longitudinal movement of the dispensing point relative to the transfer capillary (or vice versa, the longitudinal movement of the transfer capillary relative to the dispensing point, or both movements simultaneously) is variable to generate the desired pitch of the resistance wire along the transfer capillary.

Alternatively, the method can comprise steps of
a. providing a transfer capillary, and at least one resistance wire to be wound around the transfer capillary;
b. moving the wire dispensing point at a constant velocity along the length of the transfer capillary, while simultaneously rotating the transfer capillary at a rotational speed that is adjustable so as to generate the desired pitch of the resistance wire along the transfer capillary.

In a further alternative, to generate the desired pitch of the resistance wire along the transfer capillary, the method can comprise both of the foregoing approaches, i.e. varying along the length of the capillary the velocity of relative movement of the wire dispensing point and the transfer capillary and simultaneously rotating the transfer capillary at a rotational speed that is adjustable.

The transfer capillary can be any suitable transfer capillary, as described in the foregoing, e.g. it can be a transfer capillary that can comprise a metal tubing with an inert coating on its inner surface, such as a stainless steel tube, nickel tube, or tube of other suitable metal or metal alloy.

The transfer capillary can have pre-formed grooves along the length thereof, the grooves being formed in a spiral fashion along the length of the transfer capillary that matches the intended pitch of the resistance wire. The grooves can be used to aid in the positioning of the wire during its dispensing. Therefore, the method can include providing such a capillary for winding a wire around it.

There can also be provided a glue to secure the resistance wire to the transfer capillary. The glue can preferably be a high temperature glue that can tolerate long-term operating temperatures of the transfer line, e.g. temperature in the range of about 200° C. to about 350° C. As an example, high temperature silicone rubber sealant could be used, which has a −65° C. to +300° C. temperature range. The method can therefore further comprise using high temperature glue to secure position of the resistance wire on the transfer capillary.

The transfer line in accordance with the invention can be used in particular when connecting analytical systems comprising gaseous samples wherein temperature stability and/or temperature control is important. Accordingly, the invention also provides analytical systems that include a transfer line as described herein, such as systems that include a gas-chromatograph and an optical spectrometer or systems that include a gas chromatograph and a mass spectrometer. Such systems can include any transfer line as described in the foregoing, and may also include one or more power supplies, controllers, temperature sensors and temperature controllers, etc., including those described in the foregoing.

Analytical systems can for example be a gas chromatography—mass spectrometry (GC-MS) system, that can comprise a gas chromatograph, one or more transfer line as described herein, and a mass spectrometer, and wherein the system and transfer line have connection means such that the transfer line has an entry end that can be fluidly connected to the gas chromatograph and an exit end that can be fluidly connected to the mass spectrometer. Thus a sample can flow continuously from the gas chromatograph, via the transfer line, into the mass spectrometer, especially the ion source thereof.

The system can also comprise one or more power supplies, temperature sensors and temperature controllers, so as to provide power to, and be able to regulate the temperature of, the transfer line. Such power lines, sensors and controllers can be as described in the foregoing.

For example, a temperature control unit and a power supply for regulating temperature in the transfer line can be part of an oven control unit of the gas chromatograph for controlling the temperature of a GC oven in which the gas chromatograph is housed. The oven control unit can be operable to synchronously ramp the temperature of the flexible transfer capillary and the temperature of the GC oven, such that the transfer capillary and GC oven have substantially the same temperature.

The temperature sensor can be calibrated such that its reading or readback is corrected for the ratio of, or difference between, the temperature inside the transfer line and the apparent temperature at the sensor position over the relevant temperature range. In other words, even in the case where the temperature sensor does not provide an accurate measurement of the temperature within the transfer capillary, its reading can be calibrated based on a determination of the true temperature in the transfer capillary for any given setting, and the reading or readback of the temperature sensor can be adjusted accordingly during normal operation. Such correction can be based on the ratio of, or the difference between, the temperature inside the transfer line and the apparent or measured temperature at the sensor position in the transfer line within the temperature range of operation. If needed, such calibration can be performed for different temperature ranges and an applicable correction applied for any given temperature range.

The above features along with additional details of the invention, are described further in the examples below, which are intended to further illustrate the invention but are not intended to limit its scope in any way.

BRIEF DESCRIPTION OF THE DRAWINGS

The skilled person will understand that the drawings, described below, are for illustration purposes only. The drawings are not intended to limit the scope of the present teachings in any way.

FIG. 5 shows the contribution of the first (A) and second (B) layers of resistive wire to the temperature profile of the transfer line.

FIG. 8 shows effects of the choice of transfer line on analytical resolution in GC-MS. In (A) a chromatogram using a prior art transfer line is shown, while in (B) a chromatogram obtained using a transfer line according to the invention is shown.

DESCRIPTION OF VARIOUS EMBODIMENTS

In the following, exemplary embodiments of the invention will be described, referring to the figures. These examples are provided to provide further understanding of the invention, without limiting its scope.

In the following description, a series of steps are described. The skilled person will appreciate that unless required by the context, the order of steps is not critical for the resulting configuration and its effect. Further, it will be apparent to the skilled person that irrespective of the order of steps, the presence or absence of time delay between steps, can be present between some or all of the described steps.

Figure 1:
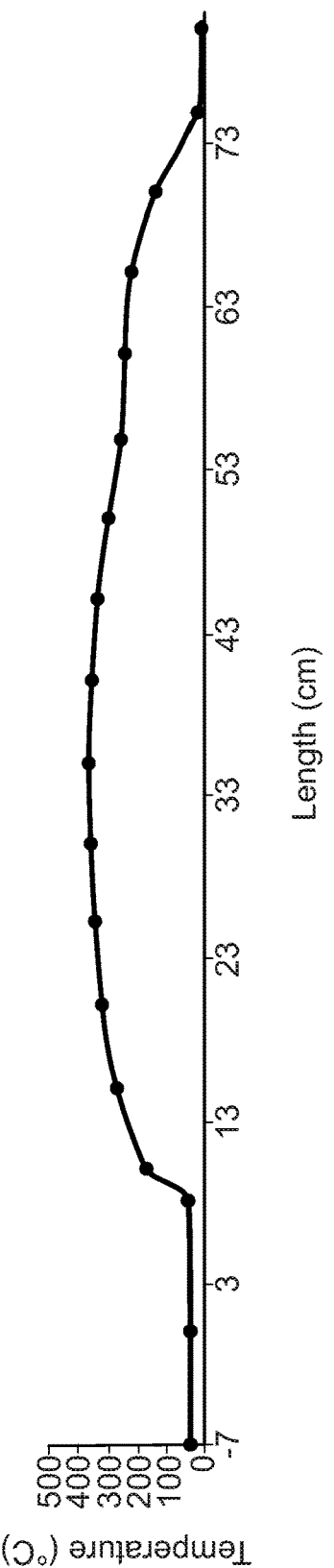
FIG. 1 shows temperature profiles along a prior art transfer line (A), and an improved prior art transfer line (B), wherein the ends of the line have added thermal insulation.

Turning to FIG. 1, temperature profiles of a prior art transfer line is illustrated. Typical prior art transfer lines suffer from the disadvantage of having steel connectors at their ends. In the case where these steel connectors are not insulated, there will be significant heat loss, due to the high thermal conductivity of the connectors. This is shown by the temperature profile in FIG. 1, where a very large temperature drop occurs at both ends of the transfer line, from the temperature of about 320° C. in the middle of the line. The temperature drop results in significant heat loss towards both ends of the transfer line, which results in significant peak broadening during a typical GC-MS analysis.

Figure 2:
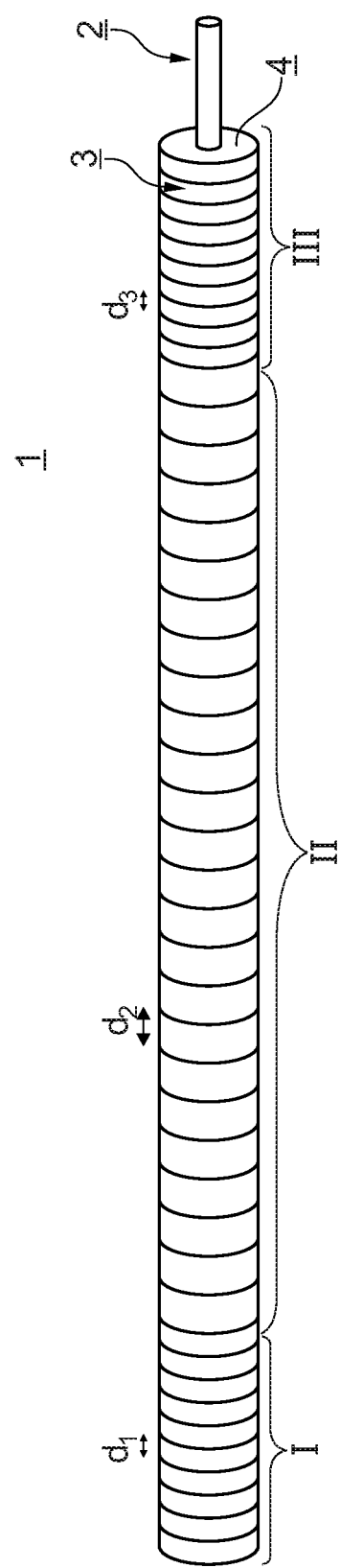
FIG. 2 shows a side view of an inner tube of a transfer line in accordance with the invention. A coated resistive wire (lead) is wound around the inner tube. Shown are three zones (I, II, III) in each of which the windings have a pitch of d1, d2 and d3, respectively.

A solution for providing a uniform temperature profile along a transfer line is illustrated in FIG. 2. A transfer line 1 is illustrated, having a tube or capillary 4 comprising a thermally conducting material, typically a metal tube that is coated on its inner surface with an inert material, such as a Ni tube that is coated with an inert silicon-based coating, such as Sulfinert™. It is an important feature of the tube that it has a low thermal mass and is flexible (low bending radius) as herein described. When in place, the tube 4 encloses an end portion of a GC column capillary 2 that is inserted into the transfer line. An annular space lies between the inner surface of tube 4 and the outer surface of the GC column capillary 2, e.g. for flow of a gas as described below. In this embodiment, the GC capillary is inserted into the transfer line so as to extend close to the end of the transfer line, leaving about 5 to 10 cm distance to the end the transfer line on the mass spectrometer end. However, trials of the setup have shown that it is also possible to obtain a high-quality chromatogram when the GC capillary is inserted just a short distance inside the entry end of the tube 4, such as within 2-5 cm, 2, 3 or 4 cm. A resistive wire 3 is wound around the thermally conducting tube 4 in a spiral fashion. The winding of the wire has a pitch d3 in the entry end zone (entry zone III), a pitch d1 towards the opposite end of the tube (end zone I), that is smaller than the pitch d2 in the middle of the tube (central zone II). The decreased pitch at the ends provides for increased heating towards the end of the tube, to compensate for heat loss at the ends, and thereby provide a uniform heat across the tube 1. The pitch d1, d2, and d3 can be adjusted as needed, depending on the material used in the tube, the length of the tube, its isolation and connections at either end, so as to provide appropriate temperature across its length during normal operation. Each end or entry zone can occupy 10 to 40% of the total length of the transfer capillary. For example, for a 50 cm transfer line, the end or entry zone may occupy 5-20 cm of the transfer line.

Figure 3:
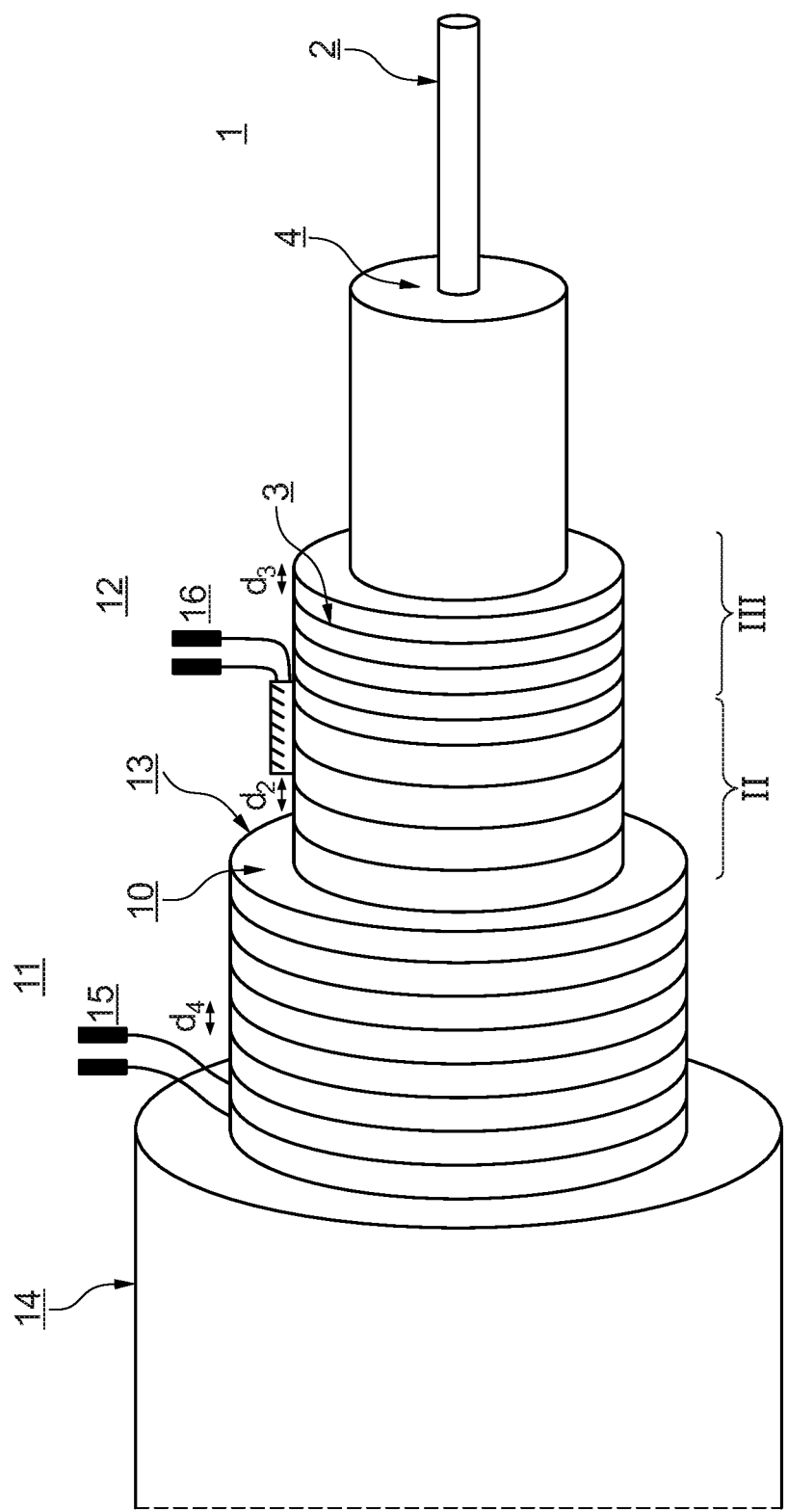
FIG. 3 shows a side view of a transfer line according to the invention. Shown is a GC column that is inserted into the inner tube of the transfer line, along which two layers of resistive wire are wound (separated by a sleeve of electrically insulating material such as fiberglass), a first layer having zones (II, III) with varying pitch (d2, d3), and a second layer with a uniform pitch (d4). The tube is encapsulated by a thermally insulating layer.

The resistive wire 3 can also be wound in two layers or windings around the inner tube 4. A transfer line featuring such double winding is illustrated in FIG. 3. The GC capillary 2 is enclosed by a thermally conducting tube 4. The resistive wire is wound around the tube 4 (which is covered with a sleeve of electrically insulating material such as fibreglass) in two layers. The first layer is provided by winding the wire 3 such that there is a smaller pitch d3 towards the end of the tube 1 than towards its middle (d2). A smaller pitch d1 is preferably also provided at the other end of the tube, which is not shown in this illustration.

A second layer/winding of the wire is provided, the second winding being of uniform pitch d4 and enclosing the first winding. A sleeve 13 of electrically insulating material such as fiberglass is provided between the two windings. Preferably, the wires are also coated with an electrically insulating material, such as a Kapton film. Encapsulating the outer winding is a layer of thermally insulating material, such as a glass wool sleeve.

Figure 4:
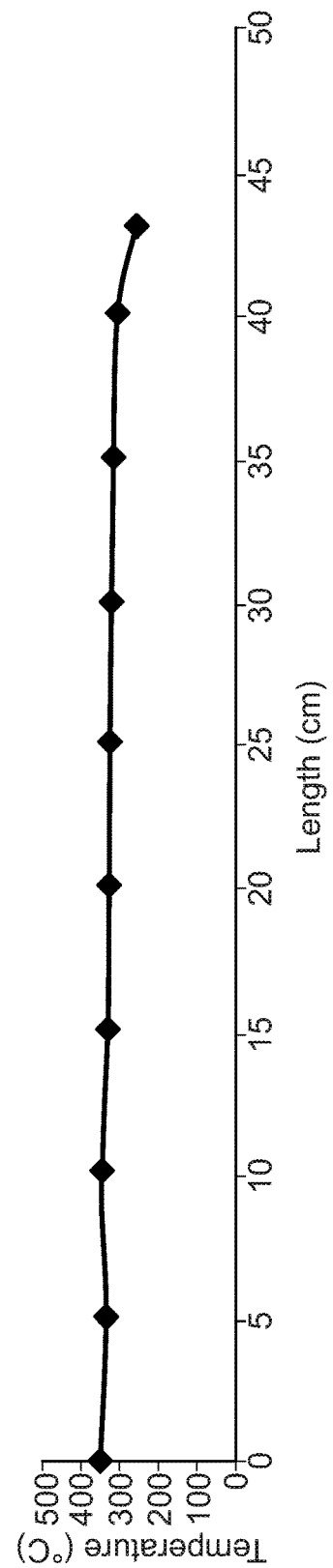
FIG. 4 shows temperature profile of a transfer line in accordance with the invention.

The transfer line provides a very stable temperature profile along its length. Thus, as illustrated in FIG. 4, when heated to about 320° C., the temperature along the transfer line is very constant, with only minor deviations at the ends of the transfer line. Overall, the temperature fluctuation along the line has a standard deviation of only about 21° C., which corresponds to a relative standard deviation of about 6.7%.

To further illustrate the benefits of having two windings of the resistive wiring, the first being of uneven pitch (denser towards the ends) and the second being of uniform pitch, the data shown in FIG. 5 indicate how each winding contributes to the temperature profile. Thus, in FIG. 5A, the temperature profile of the transfer line when only the first winding is applied is shown. Although overall quite uniform, the temperature profile shows a slight peak close to either end, with a small roughly symmetrical dip centering on the middle of the transfer line. By contrast, the temperature profile of only the second line is indicated in FIG. 5B. The profile has temperature dips towards either end, with an elevated temperature in between the ends, which has a peak in the middle of the transfer line. Thus, the second winding can be seen to stabilise and equalise the temperature profile along the transfer line and compensate for slight deficiencies in the temperature profile of the first wire winding.

The two resistive wire windings complement each other, the overall effect of both being as indicated in FIG. 4. The slight peak at the ends of the column, resulting from the first winding, is compensated by the dip due to the second winding, and vice versa towards the middle of the transfer line. The overall result is that of a transfer line with a very uniform temperature profile, as indicated in FIG. 4.

Figure 6:
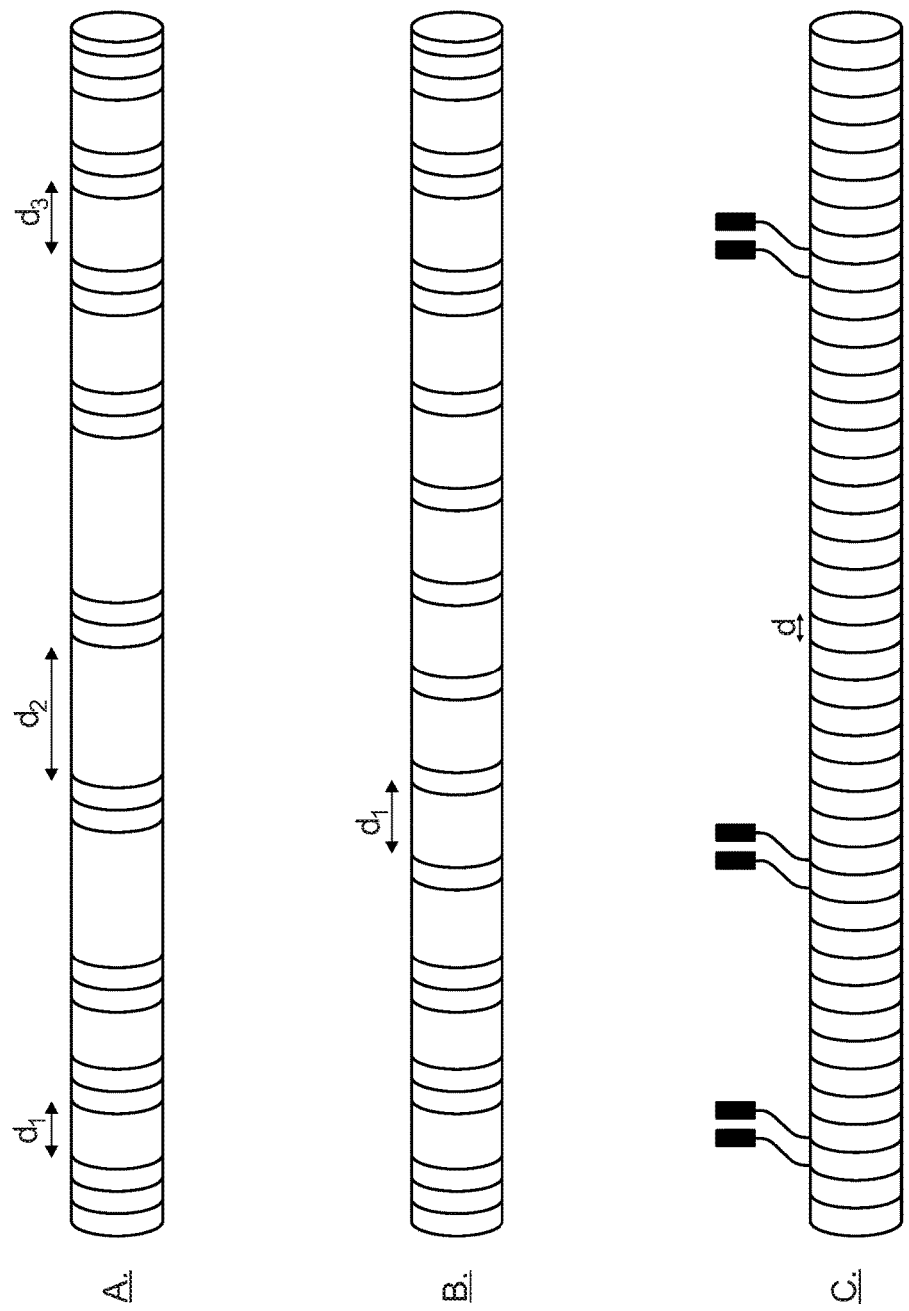
FIG. 6 shows a schematic representation of three alternative embodiments, by which the temperature along the transfer line can be varied. (A) A pulsed width modulation of the wire winding, wherein periodically spaced coil units are repeated at shorter distance within zones that are proximal to either end of the transfer line; (B) a variation of a pulsed width modulation, wherein the coil unit width is varied along the transfer line; (C) a configuration in which there are three separate wires along the transfer line, providing for the possibility to vary the power applied to each wire to generate variable heating along the length.

Alternative embodiments for achieving variable heating along the transfer line are illustrated in FIG. 6. In A, a transfer tube is shown, having a wire wound around it in a so-called pulsed width configuration (periodically spaced, relatively short units of wound wire ("unit coil")). The unit coil is relatively short compared to the whole transfer line length. Thus, there is a unit coil (indicated by three windings that are repeated at regular intervals) that is repeated with a first distance d1 between units towards one end of the tube, a second distance d2 in a central segment of the tube and a third distance d3 towards the other end of the tube. By having the distance d2 greater than d1 and/or d3, there can be decreased thermal transfer by the coil in the central region of the tube than at either end of the tube, to compensate for the greater heat loss at the respective ends.

In B, an alternative embodiment is shown. Here there are two different types of "unit coil" repeated at a fixed interval d1 along the tube. The first unit, which is repeated at both ends of the tube, is wider (more windings) than the second unit, which is repeated in the central region of tube. The overall effect is comparable to that in A, i.e. greater heat transfer at the ends of the tube than in its middle.

A third alternative embodiment is shown in C, where three wires are shown being wound around the tube. A first wire is wound at one end of the tube, a second wire is wound at the other end and a third wire is wound in the central region of the tube. By varying the power that is applied to the wires, the heating from each wire can be varied at will, for example by providing greater heat at the ends of the tube by applying greater power.

Transfer lines in accordance with the invention can be used in instrument applications that require connections between components at a constant temperature. For example, the transfer line can be very useful for connecting a gas chromatograph (GC) to a mass spectrometer or an optical spectrometer. In such applications, the GC column servers the function to separate different components of a sample that is injected, and the downstream mass spectrometer and/or optical spectrometer can be used to detect components of the sample as they are delivered by the GC column and/or to provide additional separation of sample components.

Figure 7:
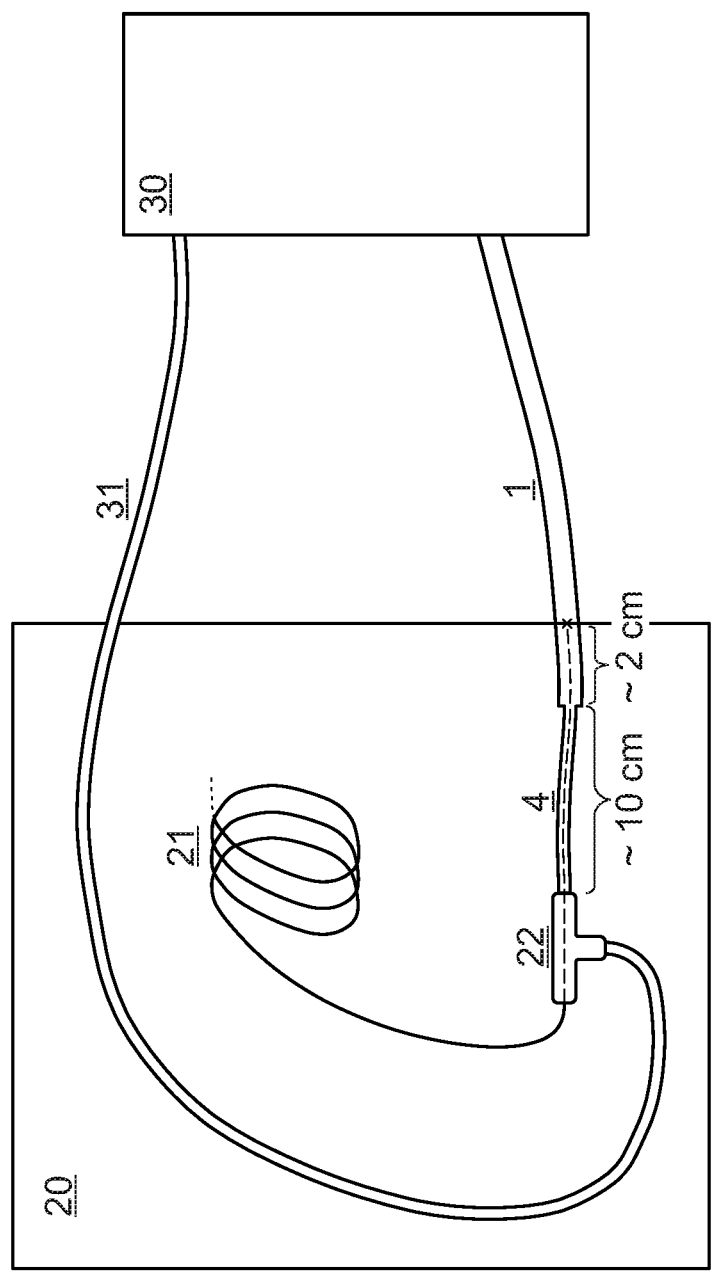
FIG. 7 shows a schematic view of a GC-MS instrument setup that incorporates a transfer line in accordance with the invention.

An exemplary GC-MS instrument setup that utilizes the transfer line is illustrated in FIG. 7. Shown is a gas chromatograph 20, that contains a GC column 21 that is typically provided in a thermally controlled space (e.g., a GC oven). The GC column is connected to the transfer tube 4 of transfer line 1 via a gas-tight T-connector 22. The GC column makes a gastight connection with the T-connector on one side and extends through the connector and into the transfer tube 4 that is connected to the opposite end of the T-connector. In this embodiment, the GC-column extends about 12 cm into the transfer capillary, 10 cm of the transfer capillary extends out of the heated entry zone of the transfer line and is positioned within the thermally controlled space (oven cavity) of the GC. Thus the GC column extends in this configuration about 2 cm into the heated region of the transfer line. A gas line 31, for providing argon gas (Ar) into the transfer line, is also connected to the T-connector. At its other end, the gas line 31 is connected to a gas supply of a mass spectrometer. The gas line can be made from any suitable inert material. For example, the tube can be made from sulfinert-coated nickel. The length of the tube 4 of the transfer line in this example is 50 cm. The typical diameter ranges of GC columns is ID=0.1-0.25 mm, OD=0.32 mm. The diameter (ID and OD) of the tube 4 in this example is ID=0.46 mm OD=1.53 mm.

During operation, Ar gas is fed through the gas tube 31 and into the tube 4 of the transfer line 1. The Ar gas line is heated by the GC oven, which ensures that the Ar gas has been heated when entering the transfer line. This is important to avoid condensation that could result from cold Ar gas entering the tube of the transfer line. The connection of the Ar gas line to the transfer line is therefore preferably inside the GC oven, so that the Ar is at the appropriate temperature when entering the transfer line. The Ar gas is fed through the tube, around the enclosed end of the GC column, towards the mass spectrometer 30. As sample gas exits the GC column, the sample gas will mix with the Ar gas that flows through the tube 4.

The GC column, or an inert extension thereof such as a capillary extension of the GC column, will extend into the flexible heated transfer line, i.e. into the flexible transfer capillary 4. The end of the GC column has to be at least far enough from the exit end of the flexible transfer capillary on the spectrometer side that a laminar flow of the mixture of the capillary effluent and argon gas can established before the sample mixture enters the spectrometer.

The GC column can extend to about 5-10 cm from the entry end of the transfer line, on the spectrometer side. However, it can be preferable that the GC column (or an extension of it) extend in the range of about 1 to 10 cm into the entry zone of the transfer line, preferably about 1 to 5 cm, or about 2 cm into the entry zone of the transfer line. The gas flow in the inner tube is typically about 1 L/min, which is considerably greater than gas flow through the GC column (typically about 1.6 mL/min).

The temperature of the transfer line is monitored by a temperature sensor connected to the tube and the sensor signal is sent to a control unit (not shown) of the GC which is the same control unit for controlling the GC oven that houses the GC column. Thus, the temperature of the transfer line is controllable by the computer and software connected to the GC and optionally the ICP MS, e.g. using extension control ports of the GC. It is therefore possible to control the transfer line temperature based on the temperature of the oven. In this embodiment, it is also possible to ramp the transfer line temperature synchronously with the GC oven, such that the temperature is the same or substantially the same in the GC oven and in the transfer line. Thus the transfer line can be regarded as effectively an "extension" of the GC oven.

The position of an ICP torch is optimized by three-dimensional movement of the torch. Therefore, the transfer line must be flexible so as to allow such three-dimensional movement of the IPC source and the transfer line end connected to it. The transfer line must be flexible so that such three-dimensional movement of the connected transfer line end does not put strain on the ICP source. The transfer line in accordance with the invention is adapted for this requirement, since it is both very light and highly flexible, which means that when stationary, the transfer line puts minimal strain on the ICP source, while also being flexible to allow three-dimensional movement of the ICP source with minimal resistance from the connected transfer line. The force for displacement of the exit end of the transfer line (the end that is attached to the ICP source) can be matched to be less than the actuation force of the motor driving the ICP torch. The actuation force of the motor can be different in the three dimensions (e.g., 40 N in x and y direction, 170 N in the z direction), and the transfer line can be adjusted so as to have a displacement force that is lower than along any direction of the ICP torch, such as 10 N or less.

Another advantage of the transfer line is that when not in use, the transfer line can simply be folded and put away. Further, the transfer line can be made to be fairly long for use in different applications. When the entire length of the transfer line is not needed, for example when the distance between the GC and the MS is short, the excess transfer line can be folded and put inside the cover of the instrument or wound in a spiral fashion. This is a vast improvement over many prior art transfer lines, that are heavy and inflexible, thus requiring a fixed geometry between the two instruments and also putting a high load on the ICP torch and significant strain on the torch during three-dimensional movement.

Figure 12:
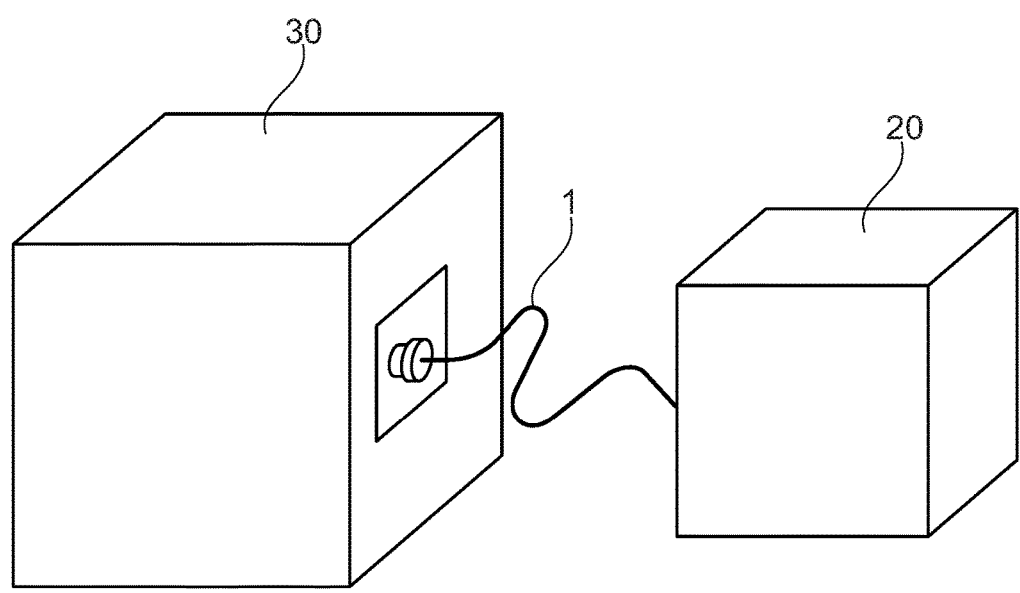
FIG. 12 shows a flexible transfer line connected between a GC system (GC) and a mass spectrometer (MS).

FIG. 12 shows schematically the flexibility of a transfer line 1 as it connects between a GC system (20) and an ICP torch inlet of a mass spectrometer (30). Its high flexibility allows the transfer line to span a range of distances between the GC and MS. The length of the transfer line being longer, typically substantially longer, than the distance between the GC and MS interfaces, along with its high flexibility means that the transfer line can be folded in order to fit the gap between systems, for example folded into a spiral-like or bent shape as shown as it connects between the two systems.

Yet another advantage of the transfer line is that due to its narrow outer diameter, the transfer line can be fed out of the GC via a very small exit slit or exit hole.

Significant analytical improvement is obtained by using the transfer line according to the invention in GC-MS applications. This improvement is illustrated by the chromatograms of a mix of organotin compounds, shown in FIG. 8. The upper chromatogram is obtained using a conventional prior art transfer line connecting a gas chromatograph and a mass spectrometer. The resolution and the signal-to-noise is less in the upper chromatogram (prior art), and as a consequence the signal of lower intensity peaks suffer, especially the later eluting peaks (p), and the analysis is unacceptable for many applications. By contrast, the lower chromatogram is obtained using a transfer line according to the invention. Vast improvement in peak width and peak separation can be seen, compared with the upper chromatograph, illustrating the improvement obtained by having a uniform temperature along the transfer line.

Figure 9:
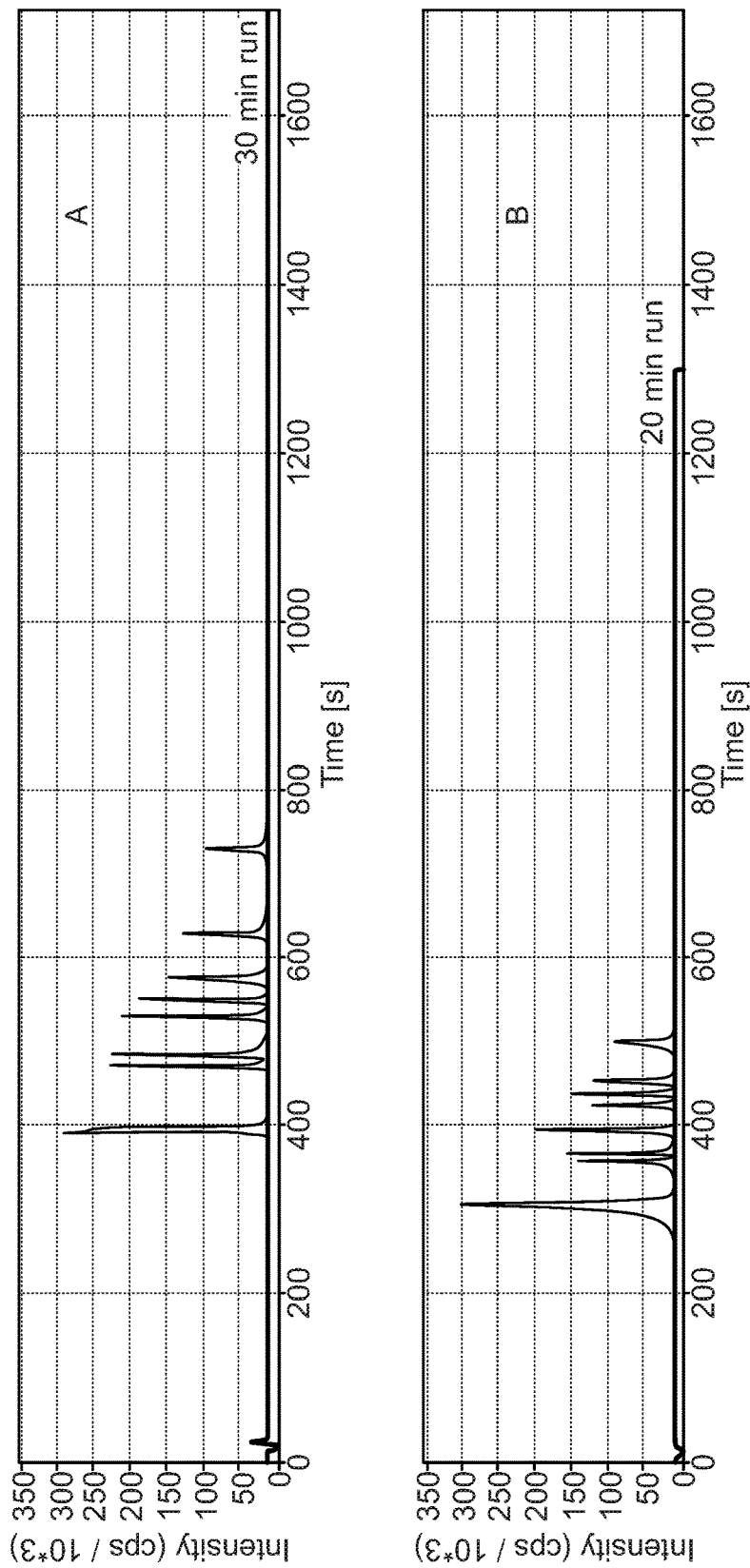
FIG. 9 shows how the run time of analytical separation procedures can be reduced using a transfer line in accordance with the invention. Shown are (A) results of 30 min run, and (B) results of 20 min run.

Another advantage of increased resolution is that the run time for any given analytical analysis can be reduced. This becomes apparent when comparing the time signals shown in FIG. 9. The upper chromatograph is obtained for a 30 minute long analytical run, whereas the lower chromatograph is obtained during a 20 minute run of identical analytical samples. Adequate peak separation is obtained in the lower chromatograph, and the reduced run time means that the throughput of the instrument is significantly increased.

Yet another advantage of the transfer line is that complex analytical procedures that require rapid temperature changes can easily be performed, such that the temperature at any given time is constant along the transfer line. For example, an analytical method may require an initial temperature (T1), rapid ramping to a second temperature (T2) for a time t2, ramping to a third temperature T3 for a third time t3, and so on. Such methods are not easily achievable using conventional transfer lines that are not adapted for rapid temperature ramping. The transfer line of the present invention therefore provides unique possibilities for applying complex analytical methods. One example of such a method (lower trace of FIG. 8 shows a chromatogram obtained with this method) involves a GC-MS application, in which the following steps are performed:
a) Initial stage at 35° C. for 1 min.
b) Ramp to 160° C. at a rate of 25° C./min.
c) Ramp to 220° C. at a rate of 12° C./min.
d) Ramp to 320° C. at a rate of 40° C./min.
e) Maintain temperature at 320° C. for 0.5 min.

By careful selection of these parameters, and being able to (a) change temperature quickly and uniformly along the transfer line length, and (b) maintain the appropriate temperature along the transfer line, separation methods can be designed as appropriate for any analytical challenge.

Figure 10:
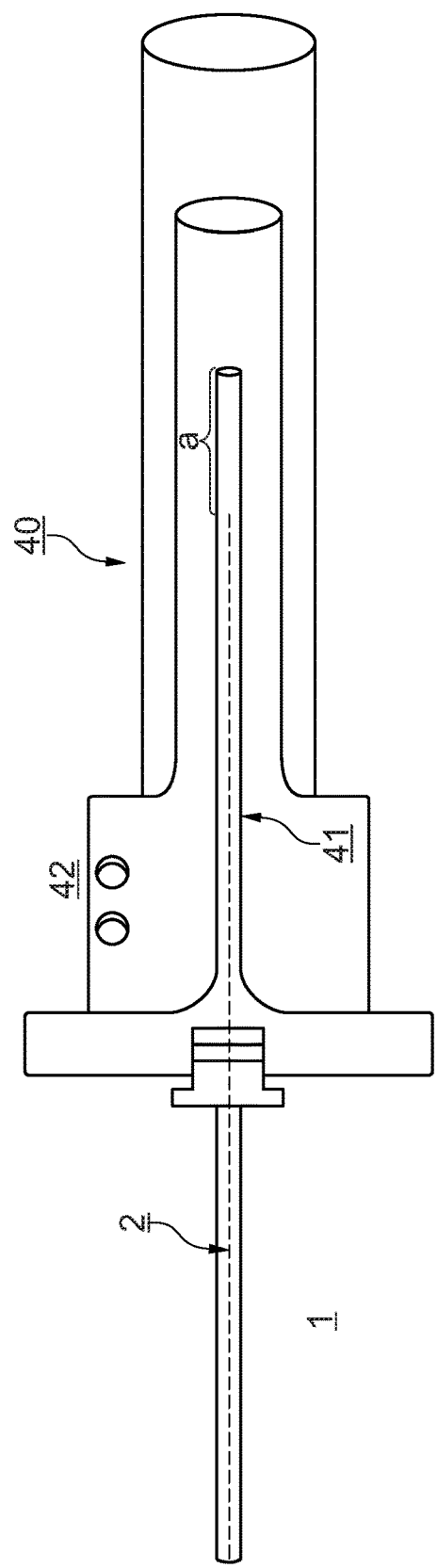
FIG. 10 shows an illustration of a possible connection between the transfer line exit end and an ICP.

FIG. 10 shows an example of a possible connection between the transfer line exit end and an ICP torch, e.g. an ICP torch of an ICP-MS. The transfer capillary 4 of the transfer line 1 preferably extends into the torch 40, inside the inner tube 41 of the torch, ending in the illustrated case (distance a) approx. 3 cm from the plasma facing end of the center tube of the torch (typically within the range 1 to 5 cm). Ports 42 for introducing plasma gas and auxiliary gas are shown.

Figure 11:
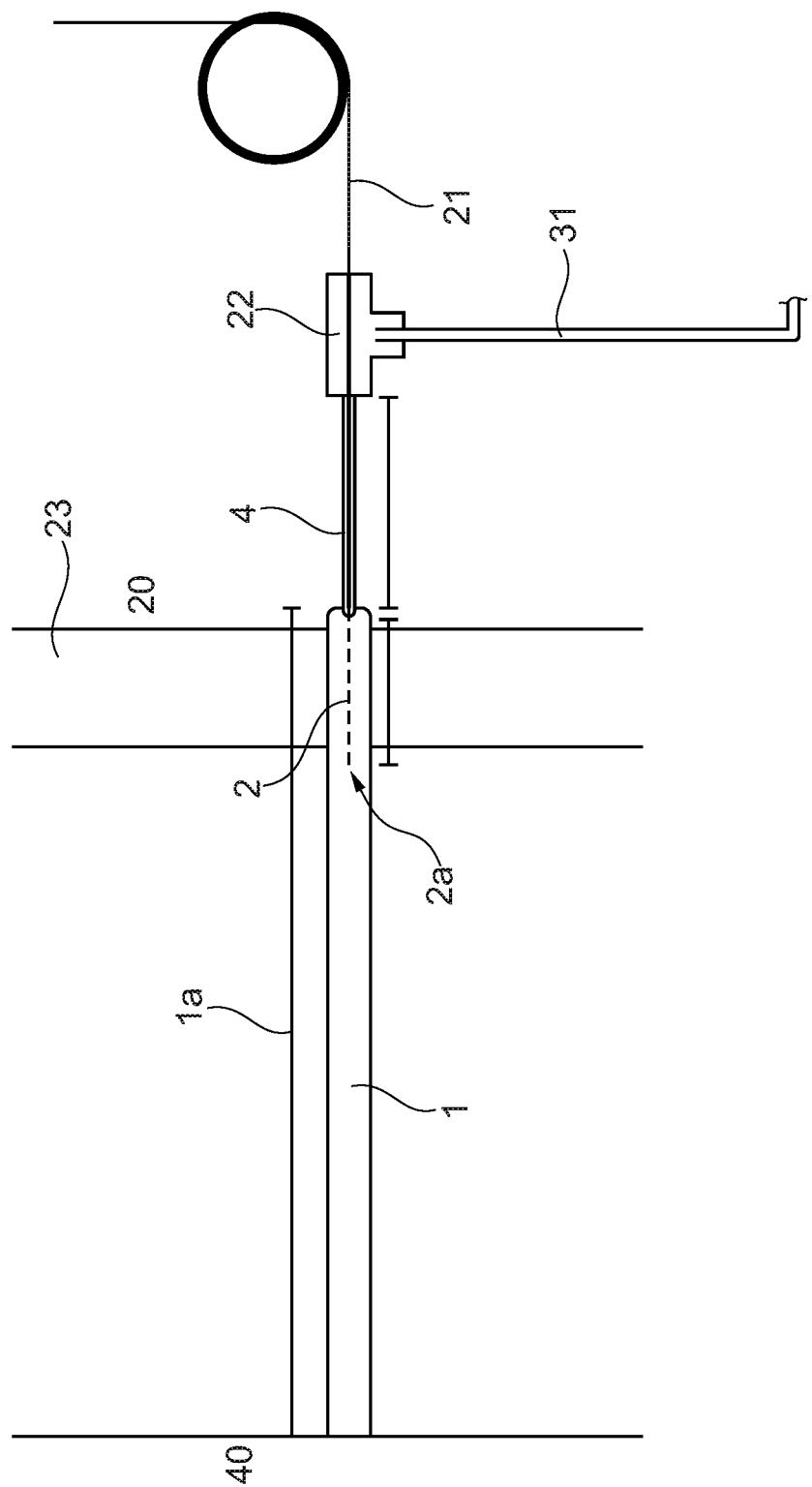
FIG. 11 shows a close-up view of the transfer line interface with a GC oven.

FIG. 11 shows a close-up view of the interface across the wall 23 of the GC oven of the gas chromatograph 20. The actively heated zone 1a of the transfer line 1 extends into the wall 23 of the GC oven, but not inside the cavity of the oven. The GC column 21 extends through the T-union 22 and into the tube 4 of the transfer line (the bare tube 4 inside the GC oven represents the non-actively heated part of the transfer line 1). Typically, within 1-5 cm of the GC column capillary 2 extends into the actively heated zone 1a and in the configuration shown above in FIG. 7 this portion of the GC column capillary is 2 cm. Argon gas is fed into the transfer line through gas line 31.

From the previous it should be apparent that the transfer line according to the present invention provides numerous advantages over transfer lines that are known in the art, including:

a. The transfer line provides a very homogeneous temperature profile with no "cold spots" that might cause condensation, nor "hot spots" that might cause deterioration of thermo labile compounds.
b. Temperature in the transfer line can be ramped very quickly due to having a low thermal mass. Similarly the temperature in the transfer line can be cooled very quickly.

The power consumption of heating the transfer line is very low compared to the bulky designs of the prior art (for example the power consumption can be about 80 W for heating up, and about 15 W for holding a temperature of 315° C.).

c. The transfer line provides for exceptional peak separation during GC-MS and/or GC-optical spectrometer analysis, as a result of the improved temperature profile.
d. The transfer line has low outer diameter and low weight, compared with transfer lines in the art that are typically heavy, bulky and inflexible.
e. The transfer line is very flexible, which is critical for connections to e.g. ICP torches that are sensitive to strain provided by external connections.
f. The energy efficiency of the transfer line is excellent.
g. The transfer line can be connected go GC electronics, providing convenient electronic temperature control, and which can for example be programmed such that the temperature profile of the transfer line mimics the temperature profile of the GC column.
h. The transfer line can be produced (and replaced) at relatively low cost due to its simple construction and low mass.

As used herein, including in the claims, singular forms of terms are to be construed as also including the plural form and vice versa, unless the context indicates otherwise. Thus, it should be noted that as used herein, the singular forms "a," "an," and "the" include plural references unless the context clearly dictates otherwise.

Throughout the description and claims, the terms "comprise", "including", "having", and "contain" and their variations should be understood as meaning "including but not limited to", and are not intended to exclude other components.

The present invention also covers the exact terms, features, values and ranges etc. in case these terms, features, values and ranges etc. are used in conjunction with terms such as about, around, generally, substantially, essentially, at least etc. (i.e., "about 3" shall also cover exactly 3 or "substantially constant" shall also cover exactly constant).

The term "at least one" should be understood as meaning "one or more", and therefore includes both embodiments that include one or multiple components. Furthermore, dependent claims that refer to independent claims that describe features with "at least one" have the same meaning, both when the feature is referred to as "the" and "the at least one".

It will be appreciated that variations to the foregoing embodiments of the invention can be made while still falling within the scope of the invention can be made while still falling within scope of the invention. Features disclosed in the specification, unless stated otherwise, can be replaced by alternative features serving the same, equivalent or similar purpose. Thus, unless stated otherwise, each feature disclosed represents one example of a generic series of equivalent or similar features.

Use of exemplary language, such as "for instance", "such as", "for example" and the like, is merely intended to better illustrate the invention and does not indicate a limitation on the scope of the invention unless so claimed. Any steps described in the specification may be performed in any order or simultaneously, unless the context clearly indicates otherwise.

All of the features and/or steps disclosed in the specification can be combined in any combination, except for combinations where at least some of the features and/or steps are mutually exclusive. In particular, preferred features of the invention are applicable to all aspects of the invention and may be used in any combination.

The invention claimed is:

1. A flexible gas chromatography transfer line for transferring a sample from a gas chromatography column into a spectrometer for analysis, having an entry end for connecting to the gas chromatography column and an exit end for connecting with a spectrometer, the transfer line comprising:
   a flexible transfer capillary for receiving therein an end portion of a gas chromatography column or a capillary connected to said end portion; and
   a flexible resistive heating arrangement, surrounding the transfer capillary;
   the resistive heating arrangement being connectable to a power supply for providing current to the resistive heating arrangement to heat the resistive heating arrangement and thereby heat the flexible transfer capillary;
   wherein the resistive heating arrangement is divided into at least one central zone and at least one exit zone,
   wherein the resistive heating arrangement is adapted to provide different heat emission per unit length in said at least one central zone than in said exit zone,
   wherein the flexible gas chromatography transfer line is foldable, a displacement force in each direction (x, y, z) needed to move the transfer line exit end when the entry end is fixed being less than 10 N.

2. The gas chromatography transfer line of claim 1 wherein the resistive heating arrangement is divided into at least one central zone, at least one exit zone, and at least one entry zone.

3. A flexible gas chromatography transfer line for transferring a sample from a gas chromatography column into a spectrometer for analysis, having an entry end for connecting to the gas chromatography column and an exit end for connecting with a spectrometer, the transfer line comprising:
   a flexible transfer capillary for receiving therein an end portion of a gas chromatography column or a capillary connected to said end portion; and
   a resistive heating arrangement, surrounding the transfer capillary, the resistive heating arrangement is divided into at least one central zone, at least one exit zone, and at least one entry zone, the resistive heating arrangement comprising resistive wire, wherein a pitch of the resistive wire in said central zone is in the range of about 5% to about 35% greater than the pitch in the at least one entry zone and the pitch in said at least one exit zone;
   the resistive heating arrangement being connectable to a power supply for providing current to the resistive heating arrangement to heat the resistive heating arrangement and thereby heat the flexible transfer capillary;
   wherein the resistive heating arrangement is divided into at least one central zone and at least one exit zone,
   wherein the resistive heating arrangement is adapted to provide different heat emission per unit length in said at least one central zone than in said exit zone,
   wherein the flexible gas chromatography transfer line is foldable, a displacement force in each direction (x, y, z) needed to move the transfer line exit end when the entry end is fixed being less than 10 N.

4. The gas chromatography transfer line of claim 1, wherein a thermal mass of the transfer line is in the range of about 5 to about 50 J/K.

5. The gas chromatography transfer line of claim 1, wherein the resistive heating arrangement comprises a resistive heating layer.

6. The gas chromatography transfer line of claim 5, wherein the resistive heating layer comprises a carrier sheet comprising electrically resistive material.

7. The gas chromatography transfer line of claim 1, wherein the resistive heating arrangement comprises a resistive wire, wherein the resistive wire comprises at least two exit zones, a first exit zone more distal from the central zone and a second exit zone more proximal to the central zone, wherein: (i) a pitch of the wire in said first exit zone is smaller than a pitch in said second exit zone, which is smaller than a pitch in the central zone, or (ii) a resistance of the wire in said first exit zone is higher than a resistance of the wire in said second exit zone, which in turn is higher than a resistance of the wire in the central zone, or (iii) a winding pattern of the wire in said first exit zone is different to a winding pattern of the wire in said second exit zone, which in turn is different to a winding pattern of the wire in the central zone.

8. The gas chromatography transfer line of claim 1, wherein said exit end is adapted to pass through a gas-tight rubber or polymer seal of a connector adapted to connect the transfer line to a mass spectrometer sample injector and/or ICP ion source.

9. The gas chromatography transfer line of claim 1, wherein the flexible transfer capillary comprises a metal tubing with an inert coating on an inner surface.

10. The gas chromatography transfer line of claim 9, wherein the inert coating is selected from silicon based coatings, other glassy coatings, and polymer coatings.

11. The gas chromatography transfer line of claim 1, wherein the flexible transfer capillary is adapted to receive a GC column such that the GC column terminates within heated zones of the flexible transfer capillary.

12. The gas chromatography transfer line of claim 1, wherein the flexible transfer capillary is adapted to connect at or near the entry end to a supply of inert carrier gas such that the carrier gas can flow in a space between the transfer capillary and a GC column in a direction towards the exit end of the transfer capillary.

13. The gas chromatography transfer line of claim 1, wherein the resistive heating arrangement terminates at a predetermined distance from the entry end of the transfer line so that, during operation, a part of the transfer capillary that is not enclosed by the heating arrangement is positioned within an oven of a gas chromatograph to which the transfer line is connected.

14. The gas chromatography transfer line of claim 1, wherein the flexible transfer capillary has an inner diameter in the range of about 0.40 mm to about 1.0 mm and an outer diameter in the range of about 1.0 mm to about 2.5 mm.

15. A flexible gas chromatography transfer line for transferring a sample from a gas chromatography column into a spectrometer for analysis, having an entry end for connecting to the gas chromatography column and an exit end for connecting with a spectrometer, the transfer line comprising:
- a flexible transfer capillary for receiving therein an end portion of a gas chromatography column or a capillary connected to said end portion;
- a resistive heating arrangement, surrounding the transfer capillary; and
- an outer heat insulating sleeve along at least a portion thereof;
- the resistive heating arrangement being connectable to a power supply for providing current to the resistive heating arrangement to heat the resistive heating arrangement and thereby heat the flexible transfer capillary;
- wherein the resistive heating arrangement is divided into at least one central zone and at least one exit zone,
- wherein the resistive heating arrangement is adapted to provide different heat emission per unit length in said at least one central zone than in said exit zone,
- wherein the flexible gas chromatography transfer line is foldable, a displacement force in each direction (x, y, z) needed to move the transfer line exit end when the entry end is fixed being less than 10 N.

16. The gas chromatography transfer line of claim 1, further comprising at least one temperature sensor to provide feedback to a temperature control unit.

17. The gas chromatography transfer line of claim 16, wherein the temperature control unit is interfaced to a power supply to control an output of the power supply to the resistive heating arrangement and thereby control a temperature of the flexible transfer capillary.

18. The gas chromatography transfer line of claim 1, wherein the transfer line and a temperature controller to which it is connected are adapted to ramp the temperature of the transfer line at a rate that is in the range of about 10° C./min to about 200° C./min.

19. The gas chromatography transfer line of claim 18, wherein the transfer line can be heated to and maintained at a temperature within a temperature range comprising at least the range from about 100° C. to about 350° C.

20. The gas chromatography transfer line of claim 1, wherein the transfer line has a bending radius of less than about 40 mm.

21. The gas chromatography transfer line of claim 1, wherein the transfer line has an outer diameter in the range of about 2 to about 10 mm.

22. The gas chromatography transfer line of claim 1, wherein the transfer line has a weight of less than about 100 g.

23. The gas chromatography transfer line of claim 1, wherein the transfer line is adapted to connect at the entry end to a gas chromatography column and at the exit end to an inductively coupled plasma (ICP) ion source.

24. The gas chromatography transfer line of claim 1, wherein the transfer line has a thermal mass per unit length in the range of about 5 to 30 J/K·m.

25. The gas chromatography transfer line of claim 1, wherein the transfer line has a specific heat capacity in the range of about 100 to 500 J/(kg·K).

* * * * *